United States Patent [19]

Hayashi et al.

[11] Patent Number: 5,679,536
[45] Date of Patent: Oct. 21, 1997

[54] CHEMILUMINESCENT ANALYTICAL METHOD

[75] Inventors: Takashi Hayashi; Riko Iwata, both of Tsukuba; Mitsuo Yamaki, Hitachi, all of Japan

[73] Assignee: Hitachi Chemical Co. Ltd., Japan

[21] Appl. No.: 504,036

[22] Filed: Jul. 19, 1995

Related U.S. Application Data

[63] Continuation of Ser. No. 135,770, Oct. 12, 1993, abandoned.

[30] Foreign Application Priority Data

Apr. 2, 1993 [JP] Japan ................................. 5-076054

[51] Int. Cl.$^6$ .................................................. G01N 33/53
[52] U.S. Cl. ..................... 435/7.9; 435/7.92; 435/7.93; 435/7.94; 435/7.95; 435/28; 435/962; 436/172; 436/825; 436/826
[58] Field of Search ..................... 435/7.9, 7.92, 435/7.93, 7.94, 7.95, 25, 27, 28, 968, 969, 962; 436/518, 524, 531, 536, 537, 172, 625, 626

[56] References Cited

U.S. PATENT DOCUMENTS

| | | | |
|---|---|---|---|
| 4,478,817 | 10/1984 | Campbell et al. | 435/7.25 |
| 4,713,324 | 12/1987 | Fox et al. | 435/4 |
| 4,810,630 | 3/1989 | Craig et al. | |
| 5,017,559 | 5/1991 | Dosako et al. | 530/360 |
| 5,106,732 | 4/1992 | Kondo et al. | 435/28 |
| 5,171,668 | 12/1992 | Sugiyama | 435/28 |
| 5,248,595 | 9/1993 | Boyer et al. | 435/7.32 |

FOREIGN PATENT DOCUMENTS

| | | |
|---|---|---|
| A 0 303 062 | 2/1989 | European Pat. Off. |
| A 0 384 271 | 8/1990 | European Pat. Off. |
| A 0 532 757 | 3/1993 | European Pat. Off. |
| A 2 233 451 | 1/1991 | Germany . |
| 63-52393 | 9/1989 | Japan . |
| A 01 289 495 | 11/1989 | Japan . |
| WO A 88 07683 | 10/1988 | WIPO . |

OTHER PUBLICATIONS

Porstmann, B. et al. Temperature dependent rise in activity of horseradish peroxidase caused by non–ionic detergents and its use in enzyme–immunoassay. Clinica Chimica Acta 109:175–181, 1981.

Thorpe, G.H. and Kricka, L.J. Enhanced Chemiluminescent Reactions Catalyzed by Horseradish Peroxidase. Methods in Enzymology 133:331–353, 1986.

J. Clin. Chem. Ckin. Biochem., 19:435–439 (1981).

*Primary Examiner*—Lora M. Green
*Attorney, Agent, or Firm*—Pennie & Edmonds

[57] ABSTRACT

A chemiluminescent method is provided for the analysis of a target. A peroxidase is first bound as a labelling substance to the target by using a target specific binding reagent. The target so labelled is isolated and then reacted with luminol, hydrogen peroxide and an enhancer in an aqueous solvent. The luminescence of light is detected and measured. The aqueous solvent contains at least one protein selected from the group consisting of skim milk and egg albumin. Preferably, the aqueous solvent also contains a non-ionic surfactant such as a polyoxyethylene ether and/or a sugar alcohol such as mannitol.

7 Claims, 5 Drawing Sheets

CHEMILUMINESCENT ANALYTICAL METHOD

This is a continuation, of application Ser. No. 08/135,770, filed Oct. 12, 1993, now abandoned.

BACKGROUND OF THE INVENTION

1) Field of the Invention

This invention relates to a chemiluminescent analytical method, and more specifically to a method for improving the performance of chemiluminescent analysis in which a peroxidase is used as a labelling substance.

2) Description of the Related Art

As a method for detecting and measuring with good sensitivity a target to be analyzed (e.g., a substance to be measured), it is known to react a target specific binding reagent such as an antibody capable of specifically bonding to the substance—said binding reagent being often labelled in advance with an enzyme such as a peroxidase—with a test sample and then to detect and measure signals produced by the catalytic action of the enzyme, e.g., a peroxidase as a labelling substance. This method is generally called "enzyme immunoassay". This enzyme immunoassay is known to include a variety of improved or modified techniques, such as the single antibody technique, the double antibody technique, the sandwich technique, the homogeneous technique and the heterogeneous technique.

To permit efficient measurement of signals produced by catalytic action of an enzyme such as a peroxidase, chemiluminescence of luminol/hydrogen peroxide catalyzed by the peroxidase is measured. In this case, a compound which can enhance the chemiluminescent reaction is frequently used as an enhancer (Method in Enzymology, 133, 331–353 (1986); U.S. Pat. No. 5,106,732).

On the other hand, the activity of a peroxidase is known to increase by the addition of a polyoxyethylene ether [Clinica Chimica Acta, 109, 177=181 (1981); J. Clin. Chem. Clin. Biochem., 19, 435–439 (1981)]. In enzyme immunoassay, it has been proposed to improve the S/N ratio or the sensitivity of measurement by incorporating a polyoxyethylene ether in a buffer (U.S. Pat. No. 4,810,630).

It is also known to treat a carrier or an antibody- (or antigen-) immobilized carrier with albumin or milk protein (Japanese Patent Application Laid-Open No. HEI 1-217266 which corresponds to U.S. Pat. No. 5,017,559) or with egg albumin (Japanese Patent Application Laid-Open No. HEI 1-224665) in advance so that any non-specific reaction of the carrier or the antibody- (or antigen-) immobilized carrier can be blocked.

Where the target of the analysis is an ultratrace substance or the like in a living body, it is still desired to develop a method having still higher sensitivity.

SUMMARY OF THE INVENTION

An object of the present invention is therefore to provide a high-sensitivity chemiluminescent analytical method.

Regarding chemiluminescent analysis in which a target labelled with a peroxidase via a target specific binding reagent is reacted with luminol, hydrogen peroxide and an enhancer in an aqueous solvent and the luminescence is detected and measured, the present inventors have proceeded with an investigation in various ways to develop a method for lowering a non-specific chemiluminescent reaction, namely, the reagent blank [which hereinafter may also be called "noise (N)"] and/or to enhance a specific chemiluminescent reaction [which hereinafter may also be called "signal {S}"] so that the S/N ratio (the ration of signal to noise) can be improved. As a result, it has been found that inclusion of at least one protein selected from skim milk and egg albumin in the aqueous solvent can substantially improve the S/N ratio and this effect can be synergistically or additionally enhanced by additional inclusion of a non-ionic surfactant and/or a sugar alcohol in combination of such a protein, leading to the completion of the present invention.

In one aspect of the present invention, there is thus provided a chemiluminescent analytical method of a target. The method comprises bonding a peroxidase as a labelling substance to the target by using a target specific binding reagent, isolating the target so labelled, reacting the labelled target with luminol, hydrogen peroxide and an enhancer in an aqueous solvent, and detecting and measuring the luminescence. The aqueous solvent comprises at least one protein selected from the group consisting of skim milk and egg albumin.

Preferably, the aqueous solvent further comprises a non-ionic surfactant such as a polyoxyethylene ether and/or a sugar alcohol such as mannitol. The aqueous solvent can preferably contain the protein at a concentration sufficient to provide an improved S/N ratio, for example, at a concentration of 0.01 wt. % to 1.0 wt. %.

The use of the peroxidase as a labelling substance in chemiluminescent analysis has made it possible to reduce non-specific luminescent reactions, that is, the reagent blank (noise) and to enhance a specific chemiluminescent reaction, that is, the signal, so that the S/N ratio (the ratio of the signal to the noise) has been increased. Further, the storage stability of the solution has also been improved. Accordingly, the reliability of measurement data has been improved.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION AND PREFERRED EMBODIMENTS

Figure 1:
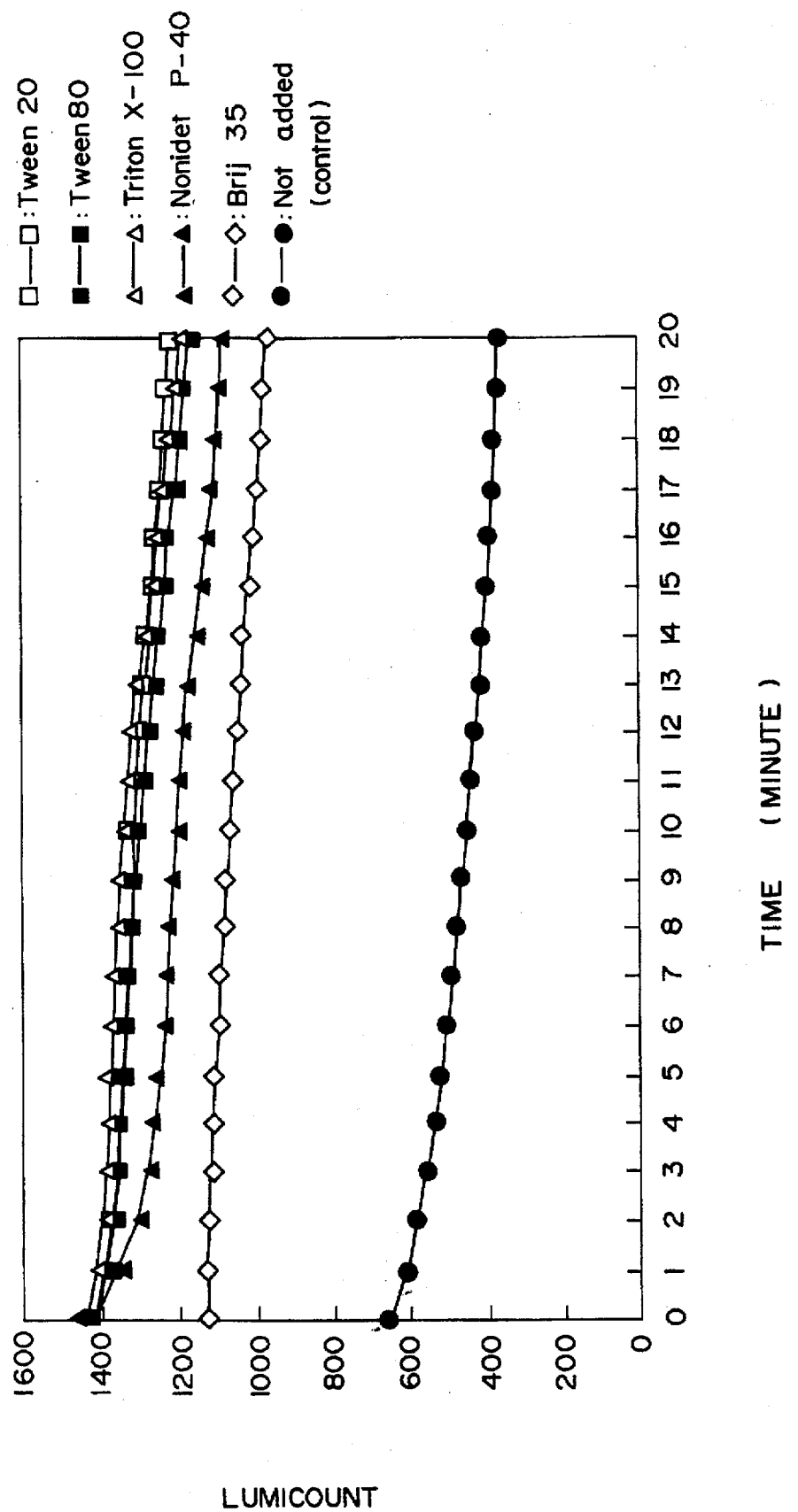
FIG. 1 is a graph illustrating time-dependent variations of signals when various non-ionic surfactants were allowed to exist (at a final concentration of 0.05%) in the presence of mannitol.

The present invention can be applied to any chemiluminescent analytical method without any particular limitation as long as a peroxidase is bound as a labelling substance to a target by using a target specific binding reagent, the peroxidase-bound target is isolated and reacted with luminol, hydrogen peroxide and an enhancer in an aqueous solvent and the luminescence is then detected and measured.

The term "target specific binding reagent" as used herein means a substance which can specifically bond to a target to be analyzed (for example, a physiologically active peptide, a hormone, a nucleic acid or the like). Where the target to be analyzed is capable of acting as an antigen, an antibody (polyclonal antibody, monoclonal antibody, an antibody fragment or the like) can become a target specific binding reagent. Where the target to be analyzed is a nucleic acid, on the other hand, its complementary (single-strand) nucleic acid or nucleic acid fragment can be a target specific binding reagent. These analytical techniques are generally classified further under the names of single-antibody immunoassay, double-antibody immunoassay, sandwich technique, western technique, DNA probe technique, etc. The present invention can be applied most preferably to the sandwich technique which uses a solid-phase carrier.

According to the present invention as applied to the sandwich technique making use of a solid-phase carrier, analysis is usually carried out in the following procedures:

(1) A first target specific binding reagent, which recognizes (can bind to) a certain particular site of a target to be analyzed, is immobilized on the solid-phase carrier to form a first target specific binding reagent immobilized carrier.

(2) The carrier is treated with a protein-containing solution (blocking treatment).

(3) The carrier so treated is washed with a washing solution.

(4) A sample is added either singly or together with an aqueous solvent, followed by incubation to form a complex of a first target specific binding reagent immobilized carrier and the target to be analyzed.

(5) The complex is washed with a washing solution.

(6) A second target specific binding reagent—which can recognize another site of the target to be analyzed, said another site being different from the certain particular site, and is labelled with the peroxidase—is added together with an aqueous solvent to form a complex of the first target specific binding reagent immobilized carrier, the target to be analyzed, the second target specific binding reagent and the peroxidase.

(7) The complex is washed with a washing solution.

(8) The complex obtained at the step (6) is reacted with an aqueous solvent which contains skim milk and/or egg albumin, and luminol, hydrogen peroxide and enhancer.

(9) The luminescence is measured.

Instead of the above step (6), the following procedures can be used:

(6-1) A second target specific binding reagent—which can recognize another site of the target to be analyzed, said another site being different from the certain particular site, and contains a reactive group such as a biotin residue—is reacted in an aqueous solvent.

(6-2) The resulting complex is washed with a washing solution.

(6-3) The complex so washed is reacted in an aqueous solvent with the peroxidase which contains a reactive group such as an avidin residue.

The skim milk usable in the present invention is milk from which the fat has been eliminated. It is also called "skimmed powder milk", "skim milk" or "non-fat milk". Commercial skim milk products can be used in general. Commercial skim milk products include, for example, "MILK DILUENT/BLOCKING SOLUTION" (product of KPL Corp.; Code No.: 50-92-01), "Block Ace" (trade mark, product of Dainippon Pharmaceutical Co., Ltd.; Code No.: UK-B25), and "Block Ace Powder" (trade mark, product of Dainippon Pharmaceutical Co., Ltd.; Code No. UK-B80).

Egg albumin usable in this invention is a protein which has been isolated from egg white and has a molecular weight of 45,000 and an isoelectric point of 4.6. Commercial products can also be used ordinarily. Illustrative commercial products include "Albumin, egg white, 5-fold crystallization product" (product of Seikagaku Kogyo Co., Ltd., Code Number: 250440), "Oval-bumin" (product of Taiyo Kagaku Co., Ltd., Code Number: 300-00711), "Albumin, produced from eggs" (product of Wako Pure Chemical Industries, Ltd.) and "Albumin chicken egg" (product of Sigma Chemical Co., Code Number: A7641).

Such skim milk or egg albumin is used at least at such a concentration that can improve the S/N ratio. In general, their concentrations are both 0.01–0.5 wt. %, preferably 0.02–0.2 wt. % in terms of their final concentrations in the reaction mixture. Concentrations lower than 0.01 wt. % are too low to effectively improve the S/N ratio while concentrations higher than 0.5 wt. % suppress the specific luminescent reaction. Concentrations outside the above range are therefore not preferred.

Mere designation of "%" will hereinafter means "wt. %" unless otherwise specifically indicated.

Illustrative of non-ionic surfactants usable in the present invention include acylsorbitan, polyoxyethylene ethers, and polyoxyethylene sorbitan esters. Usable commercial products include, for example, "Span 20" (sorbitan monolaurate), "Span 40" (sorbitan monopalmitate), "Span 60" (sorbitan monostearate), "Span 80" (sorbitan monooleate), "Span 85" (sorbitan trioleate), "Tween 20" (polyoxyethylene sorbitan monolaurate), "Tween 40" (polyoxyethylene sorbitan monopalmitate), "Tween 60" (polyoxyethylene sorbitan monostearate), "Tween 80" (polyoxyethylene sorbitan monooleate), "Tween 85" (polyoxyethylene sorbitan trioleate), "Brij 35" (polyoxyethylene lauryl ether) and "Brij 58" (polyoxyethylene cetyl ether), all products of Atlas Powder Co.; "Triton X-100" (polyoxyethylene (10) octylphenyl ether) and "Triton X-405" (polyoxyethylene (40) octylphenyl ether), both products of Rohm & Haas Co.; "Nonidet P-40" (octylphenol ethylene oxide), product of Sigma Chemical Co., Ltd.; and "Adekatol SO Series" (secondary linear alcohol ethoxylates), products of Asahi Denka Kogyo K.K.

The non-ionic surfactant is added at least at such a concentration that can improve the S/N ratio. In general, its concentration is in a range of 0.001–2.0%, more preferably in a range of 0.01–0.5% in terms of its final concentration in the reaction mixture. Neither concentrations lower than 0.001% nor those greater than 2% are significantly effective in improving the S/N ratio.

Examples of sugar alcohols usable in the present invention include sugar alcohols containing 6 to 3 carbon atoms, such as mannitol, sorbitol, galactitol, ribitol, arabitol, erythritol and glycerin. They are added at least at such a concentration that can improve the S/N ratio. In general, their concentration is in a range of 0.01–10%, preferably in a range of 0.25–2.0% in terms of their final concentration in the reaction mixture. Concentrations lower than 0.01% are too low to significantly improve the S/N ratio, while concentrations greater than 10% suppress the specific luminescent reaction. Concentrations outside the above range are therefore not preferred.

The aqueous solvent employed as a medium for the fluorescent reaction is generally water or a buffer. Illustrative buffers include various buffers commonly employed in biochemical experiments, such as phosphate buffer, borate buffer and Good's buffer. These buffers generally have a pH in a range of 5–12, preferably in a range of 7–11. pH values lower than 5 are outside the optimal pH range for the peroxidase, so that the luminescence becomes lower. pH values higher than 12, on the other hand, result in stronger luminescence which does not rely upon the activity of the peroxidase (i.e., noise).

The peroxidase used as a labelling substance is preferably a basic isozyme of horseradish. Known basic isozymes of horseradish include Forms B, C, D and E. Of these, Form C is particularly preferred.

To bond the target specific binding reagent with the peroxidase (in other words, to label the target specific binding reagent with the peroxidase), they are directly bonded together by the maleimide-hinge technique, the succinimide technique or the like where the target specific binding reagent is an antibody. As an alternative, the target specific binding reagent is provided with a chemical group such as a biotinyl group or the like, followed by the reaction with a peroxidase containing a chemical group reactive with the former chemical group, such as an avidin residue so that the target specific binding reagent is indirectly labelled.

As luminol for use in the luminescent reaction, a reagent-grade commercial product which is readily available is used after repeating recrystallization and purifying it, because such a commercial product often contains hydrazine and sulfide ions employed as raw materials.

As an enhancer for use in the present invention, any enhancer can be used insofar as it can facilitate electron transfer from hydrogen peroxide to luminol and can exhibit enhancing action. Such enhancers include 4-iodophenol, 4-bromophenol, 4-chlorophenol, 4-phenylphenol, 2-chloro-4-phenylphenol, 4-(2'-thienyl)phenol, 6-hydroxybenzothiazole, 4-[4'-(2'-methyl)thiazolyl]phenol, 4-[2'-(4'-methyl)thiazolyl]phenol, 4-(2'-benzothiazolyl) phenyl, and 3-(10-phenothiazyl)-n-propylsulfonates.

When the luminescent reaction between luminol and hydrogen peroxide is conducted by the peroxidase in the presence of such an enhancer, the enhancer forms enhancer radicals. These radicals then react with luminol so that light is emitted.

Of the additives described above, skim milk has the characteristic feature that it is effective in substantially reducing the noise level.

Egg albumin has the characteristic feature that it does not substantially affect the signal level but it is effective in reducing the noise level, stably maintaining the resulting luminescence and also enhancing the storage stability of a luminescent substrate sample solution.

The non-ionic surfactant has the characteristic feature that it does not substantially affect the noise level but is effective in increasing the signal level.

The sugar alcohol does not substantially affect the signal level but is effective in reducing the noise level.

These characteristic features of the additives will hereinafter be described by the following experiments.

EXPERIMENT 1-1

Effects of skim milk, egg albumin, proteolysate, sugar alcohol or non-ionic surfactant on a reagent blank (noise)

In wells of a module-typed microtiter plate having a reflective aluminum film deposited on an outer surface thereof, 100 µl of 50 mM sodium borate buffer of pH 10.0 (hereinafter simply called "the borate buffer") and 100 µl portions of the borate buffer, said buffer portions containing skim milk, egg albumin, the proteolysate, the sugar alcohols and the non-ionic surfactants at the corresponding final concentrations shown in Table 1, were placed respectively. Each well was added with 8 µl of a 2 mM solution of 4-[4'-(2'-methyl)thiazolyl]phenol in dimethyl sulfoxide, 50 µl of a 4 mM solution of hydrogen peroxide in the borate buffer and 50 µl of a 20 mM luminol solution, followed by stirring and mixing. The chemiluminescence (unit: lumicount) of each well was periodically measured for 20 minutes by a chemiluminescence meter ("MLR-100", trade name; manufactured by Corona Electric Co., Ltd.)

As a result, the reagent blank value of each sample remained substantially constant during the 20-minute reaction. The reagent blank values at the reaction time of 10 minutes are shown in Table 1.

TABLE 1

| Additive | Final concentration (%) | Reagent blank (lumicount) |
|---|---|---|
| Not added (control) | — | 240 |
| Skim milk | 0.05 | 50 |
| " | 0.10 | 30 |
| Egg albumin | 0.05 | 120 |
| " | 0.10 | 100 |
| Casein proteolysate | 0.05 | 140 |
| " | 0.10 | 200 |
| Mannitol | 0.25 | 120 |
| " | 0.45 | 65 |
| Sorbitol | 0.45 | 65 |
| Tween 20 | 0.05 | 233 |
| " | 0.05 | 236 |
| Triton X-100 | 0.05 | 234 |
| Nonidet P-40 | 0.05 | 239 |
| Brij 35 | 0.05 | 238 |

Skim milk significantly reduced the reagent blank, while egg albumin and the sugar alcohols intermediately lowered the reagent blank. The non-ionic surfactants such as Tween 20 gave substantially no influence to the reagent blank.

EXPERIMENT 1-2

Effects of sugar alcohol on reagent blank in the presence of both skim milk and Tween 20

In wells of a module-typed microtiter plate having a reflective aluminum film deposited on an outer surface thereof, 100 µl portions of the borate buffer and 100 µl portions of the borate buffer, the latter buffer portions containing 0.1% of skim milk and 0.2% of Tween 20, were placed respectively. Each well was added with 8 µl of a 2 mM solution of 4-[4'-(2'-methyl)thiazolyl]phenol in dimethyl sulfoxide, 50 µl of a 4 mM solution of hydrogen peroxide in the borate buffer, said 4 mM solution containing mannitol or sorbitol at the corresponding concentration shown in Table 2, and 50 µl of a 20 mM luminol solution. The experiment was thereafter conducted as in Experiment 1-1 to measure chemiluminescence (Table 2)

TABLE 2

| Sugar alcohol | Final concentration (%) | Reagent blank (lumicount) |
|---|---|---|
| Not added (control) | 0.0 | 30 |
| Mannitol | 0.25 | 15 |

TABLE 2-continued

| Sugar alcohol | Final concentration (%) | Reagent blank (lumicount) |
|---|---|---|
| " | 0.45 | 8 |
| Sorbitol | 0.45 | 8 |

In the presence of skim milk and Tween 20, both mannitol and sorbitol also lowered the reagent blank further.

EXPERIMENT 1-3

Effects of skim milk, egg albumin and proteolysate on reagent blank in the presence of mannitol In wells of a module-typed microtiter plate having a reflective aluminum film deposited on an outer surface thereof, a 100 μl portion of the borate buffer, said portion containing 0.10% (final concentration: 0.05%) or 0.2% (final concentration: 0.1%) of skim milk, egg albumin or the proteolysate shown in Table 3. Each well was added with 8 μl of a 2 mM solution of 4-[4'-(2'-methyl)thiazolyl]phenol in dimethyl sulfoxide, 50 μl of a 4 mM solution of hydrogen peroxide in the borate buffer, said 4 mM solution containing 1.0% of mannitol, and 50 μl of a 20 mM luminol solution. The experiment was thereafter conducted as in Experiment 1-1 to measure chemiluminescence (Table 3)

TABLE 3

| Protein or proteolysate | Final concentration (%) | Reagent blank (lumicount) |
|---|---|---|
| Not added (control) | 0.00 | 70 |
| Skim milk | 0.05 | 20 |
| " | 0.10 | 10 |
| Egg albumin | 0.05 | 30 |
| " | 0.10 | 24 |
| Casein proteolysate | 0.05 | 35 |
| " | 0.10 | 54 |

In the presence of mannitol, both skim milk and egg albumin also lowered the reagent blank further.

EXPERIMENT 2-1

Effects of Mannitol on Signal Level

In each well of a module-typed microtiter plate having a reflective aluminum film deposited on an outer surface thereof, 100 μl of a 100,000-fold dilution solution (diluent: the borate buffer) of anti-endothelin-1 monoclonal antibody ("MCA ET-02", trade name; product of Yamasa Shoyu Co., Ltd.) labelled with horseradish peroxidase (product of Toyobo Co., Ltd., grade: I-C), 8 μl of a 2 mM solution of 4-[4'-(2'-methyl)thiazolyl]phenol in dimethyl sulfoxide, 50 μl of a 4 mM solution of hydrogen peroxide in the borate buffer [or a 4 mM solution of hydrogen peroxide in the borate buffer, said solution containing 0.1% (final concentration: 0.25%) mannitol] and 50 μl of a 20 mM luminol solution were placed. The contents were then stirred and mixed. Using a chemiluminescence meter, chemiluminescence was measured immediately after the mixing and also upon elapsed times of 1 minute, 2 minutes, 3 minutes, 4 minutes and 5 minutes, respectively (Table 4).

The addition of mannitol made it possible to obtain stable luminescence from immediately after the initiation of the measurement. After 5 minutes had passed since the initiation of the measurement, no significant difference was observed between both the samples.

TABLE 4

| | Signal level (lumicount) | |
|---|---|---|
| Time (min.) | Not added (Control) | 0.25% Mannitol |
| 0 | 1382 | 1495 |
| 1 | 1461 | 1544 |
| 2 | 1480 | 1553 |
| 3 | 1488 | 1546 |
| 4 | 1489 | 1529 |
| 5 | 1485 | 1511 |

EXPERIMENT 2-2

Effects of non-ionic surfactant on reagent blank, signal level and S/N ratio in the presence of mannitol In each well of a module-typed microtiter plate having a reflective aluminum film deposited on an outer surface thereof, 100 μl of the borate buffer or 100 μl of a 100,000-fold dilution solution (diluent: the borate buffer containing the corresponding non-ionic surfactant shown in Table 5) of the antiendothelin-1 monoclonal antibody labelled with the horseradish peroxidase were placed, followed by the successive addition of 8 μl of a 2 mM solution of 4-[4'-(2'-methyl)thiazolyl]phenol in dimethyl sulfoxide, 50 μl of a 4 mM solution of hydrogen peroxide in the borate buffer, said 4 mM solution containing 1.0% of mannitol, and 50 μl of a 20 mM luminol solution. The contents were then stirred and mixed. Using a chemiluminescence meter, chemiluminescence was measured for 20 minutes.

Table 5 presents the reagent blanks (noise levels), signal levels and S/N ratios measured upon an elapsed reaction time of 10 minutes. FIG. 1 diagrammatically illustrates the time-dependent variations in signal level when the respective non-ionic surfactants were contained (at the final concentration of 0.05%) and were not contained (controls). Incidentally, each reagent blank remained substantially constant during the reaction for 20 minutes.

TABLE 5

| Surfactant | Final concentration (%) | Noise (lumicount) | Signal (lumicount) | S/N ratio |
|---|---|---|---|---|
| None (control) | — | 278 | 450 | 1.62 |
| Tween 20 | 0.02 | 238 | 1311 | 5.51 |
| | 0.05 | 302 | 1363 | 4.51 |
| | 0.10 | 334 | 1303 | 3.90 |
| Tween 80 | 0.02 | 303 | 1293 | 4.27 |
| | 0.05 | 402 | 1354 | 3.37 |
| | 0.10 | 362 | 1257 | 3.47 |
| Triton X-100 | 0.02 | 366 | 1331 | 3.64 |
| | 0.05 | 390 | 1357 | 3.48 |
| | 0.10 | 270 | 1233 | 4.57 |
| Nonidet P40 | 0.02 | 339 | 1197 | 3.53 |
| | 0.05 | 340 | 1195 | 3.51 |
| | 0.10 | 404 | 1283 | 3.18 |
| Brij 35 | 0.02 | 290 | 1058 | 3.65 |
| | 0.05 | 310 | 1155 | 3.73 |
| | 0.10 | 348 | 1229 | 3.53 |

From the results of Table 5 or FIG. 1, it is understood that compared with the same not added with any of the non-ionic surfactants (control), the samples added with Tween 20, Tween-80, Triton X-100, Nonidet P-40 or Brij 35 had almost the same value in reagent blank but their signal levels increased as much as 4–5 times and their S/N ratios were also higher.

EXPERIMENT 2-3

Effects of co-existence of skim milk and non-ionic surfactant on reagent blank, signal level and S/N ratio in the presence of mannitol In each well of a module-typed microtiter plate having a reflective aluminum film deposited on an outer surface thereof, 100 µl of the borate buffer or 100 µl of a 100,000-fold dilution solution (diluent: the borate buffer containing skim milk at a final concentration of 0.05% and the corresponding non-ionic surfactant shown in Table 6 at a final concentration of 0.05%) of the antiendothelin-1 monoclonal antibody labelled with the horseradish peroxidase were placed, followed by the addition of 8 µl of a 2 mM solution of 4-[4'-(2'-methyl)thiazolyl]phenol in dimethyl sulfoxide, 50 µl of a 4 mM solution of hydrogen peroxide in the borate buffer, said 4 mM solution containing 1.0% of mannitol, and 50 µl of a 20 mM luminol solution. The contents were then stirred and mixed. Using a chemiluminescence meter, chemiluminescence was measured for 20 minutes.

Figure 2:
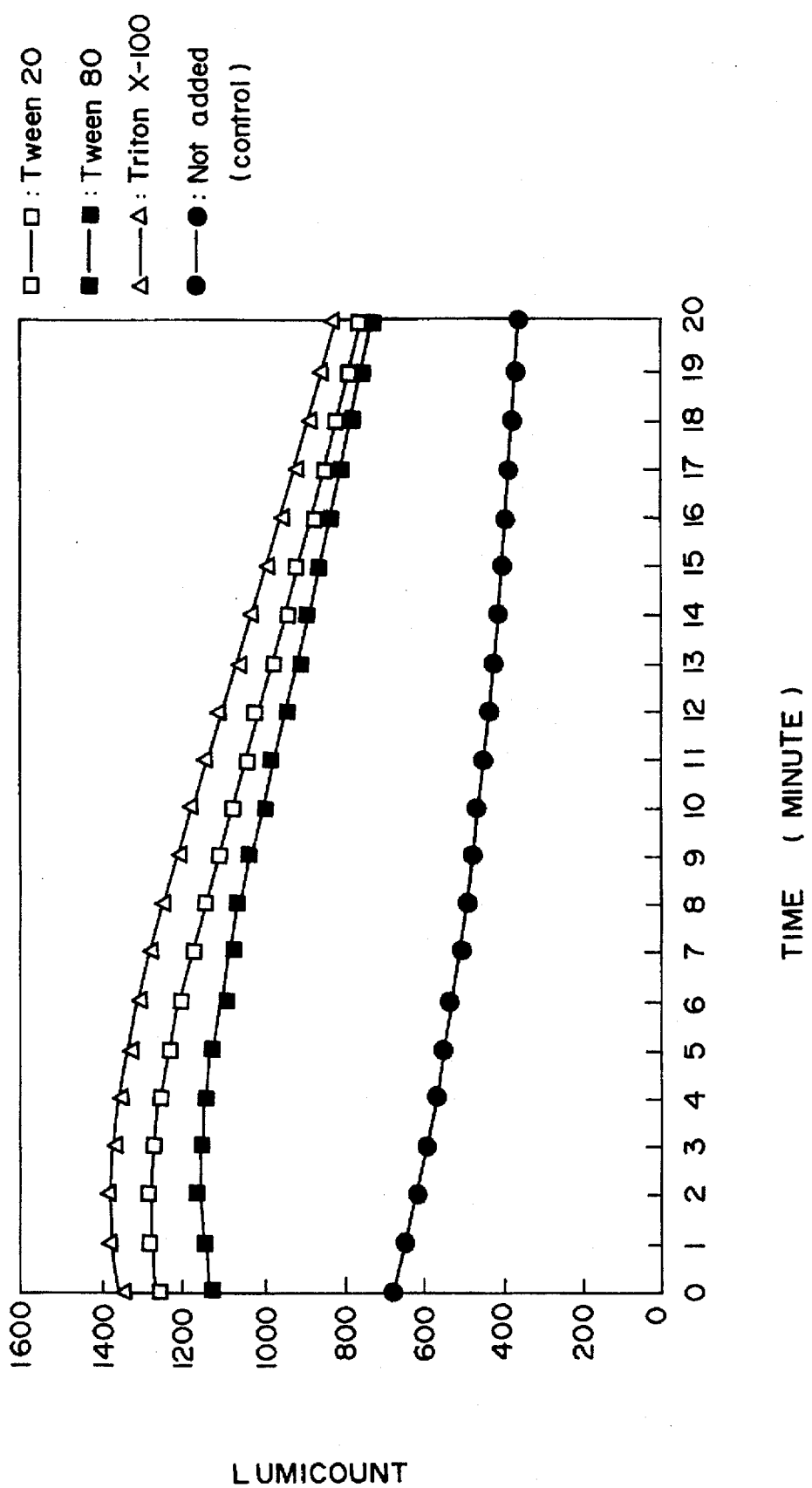
FIG. 2 is a graph depicting time-dependent variations of signals when both skim milk and non-ionic surfactants were allowed to exist (at a final concentration of 0.05%) in the presence of mannitol.

Table 6 presents the reagent blanks (noise levels), signal levels and S/N ratios measured upon an elapsed reaction time of 10 minutes. Further, FIG. 2 diagrammatically illustrates the time-dependent variations in signal level at that time. Incidentally, each reagent blank remained substantially constant during the reaction for 20 minutes.

It is understood (from Table 6 and FIG. 2) that the combined use of skim milk and Tween 20, Tween 80 or Triton X-100 increased the luminescence 3–7 times as much as that of the surfactant-free sample (control) and coupled with the noise-reducing effect of skim milk, the S/N ratio about 20 times as much as that of the surfactant-free sample (control).

TABLE 6

| Skim milk or surfactant | Noise* | Signal* | S/N ratio |
| --- | --- | --- | --- |
| None (control) | 254 | 467 | 1.84 |
| Skim milk + Tween 20 | 27 | 1075 | 39.81 |
| Skim milk + Tween 80 | 27 | 994 | 36.81 |
| Skim milk + Triton X-100 | 27 | 1179 | 43.67 |

*Unit: lumicount

EXPERIMENT 3-1

Effects of co-existence of egg albumin and non-ionic surfactant on the stable maintenance of signal level in the presence of mannitol In each well of a black-colored module-typed microtiter plate (manufactured by Dynatec, Inc.), 100 µl of a 100,000-fold dilution solution (diluent: the borate buffer containing egg albumin at a final concentration of 0.05% and Tween 20 at a final concentration of 0.05%) of the antiendothelin-1 monoclonal antibody labelled with the horseradish peroxidase, 8 µl of a 2 mM solution of 4-[4'-(2'-methyl)thiazolyl]phenol in dimethyl sulfoxide, 50 µl of a 4 mM solution of hydrogen peroxide in the borate buffer and 50 µl of a 20 mM luminol solution were placed. The contents were then stirred and mixed. Using a chemiluminescence meter, chemiluminescence was measured periodically for 20 minutes.

Figure 3:
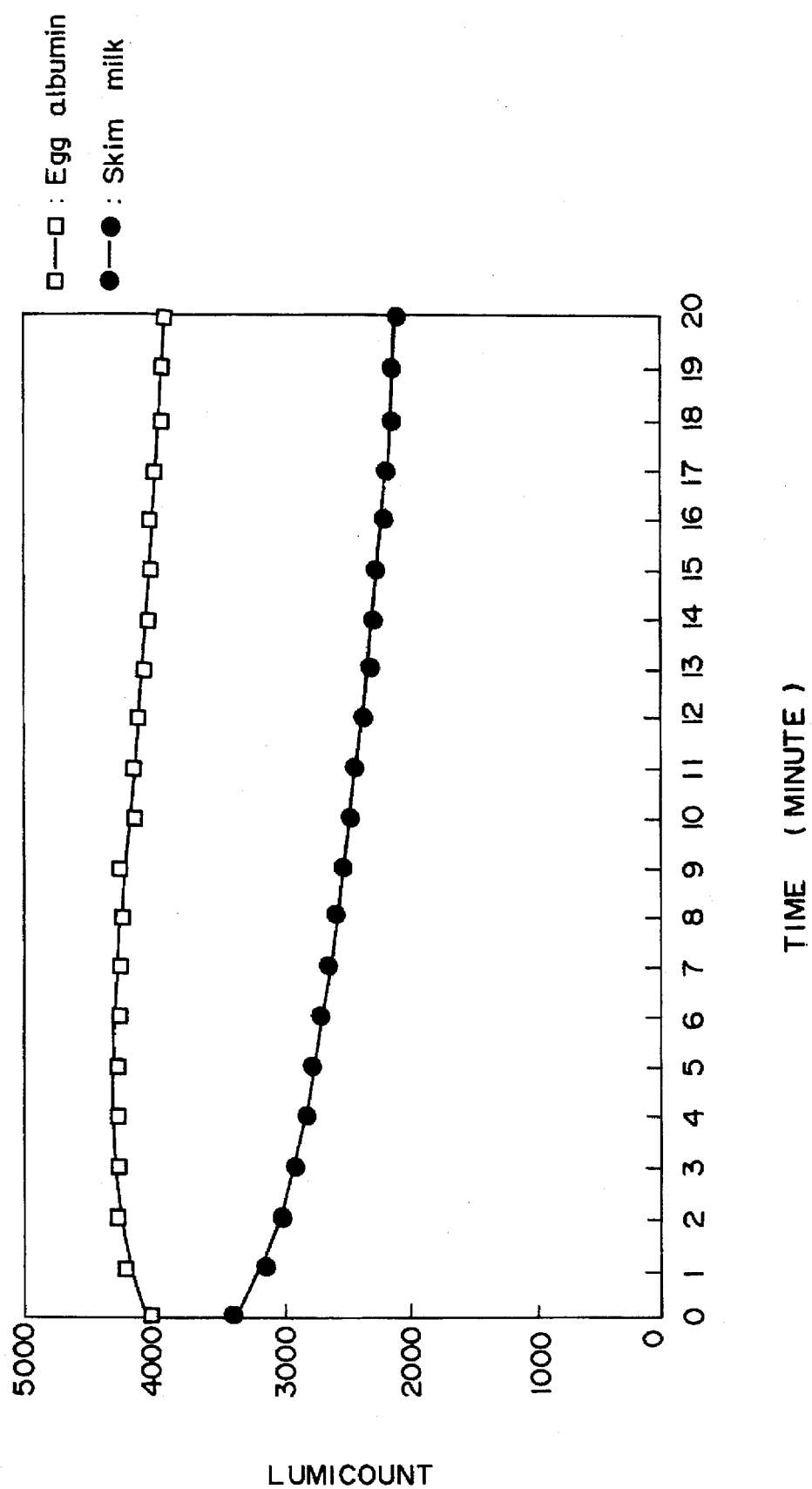
FIG. 3 is a graph showing time-dependent variations of signals when egg albumin or skim milk was allowed to exist (at a final concentration of 0.05%) in the presence of mannitol and a non-ionic surfactant.

For the sake of comparison, the above procedures were repeated in a similar manner except that in place of egg albumin, skim milk was used at the same concentration (final concentration: 0.05%). Time-dependent variations of the signal levels are shown in FIG. 3. It has been found that the addition of egg albumin allows a signal level to remain more stably for a longer time than skim milk.

EXPERIMENT 3-2

Storage stability of hydrogen peroxide sample solution containing egg albumin or skim milk An egg-albumin-containing hydrogen peroxide sample solution and a skim-milk-containing hydrogen peroxide sample solution were compared in storage stability.

The egg-albumin-containing hydrogen peroxide solution was prepared by diluting mannitol, egg albumin, Tween 20 and hydrogen peroxide with the borate buffer as needed so that they were contained at concentrations 1%, 0.15%, 0.1% and 4 mM, respectively. The skim-milk-containing hydrogen peroxide sample solution, on the other hand, was prepared by diluting mannitol, skim milk, Tween 20 and hydrogen peroxide with the borate buffer as needed so that they were contained at concentrations of 1%, 0.075%, 0.1% and 4 mM, respectively.

Both the hydrogen peroxide solutions were stored at 37° C. Predetermined amounts were periodically sampled out from them. Those samples were each subjected to chemiluminescent reaction, whereby its luminescence was measured.

Figure 4:
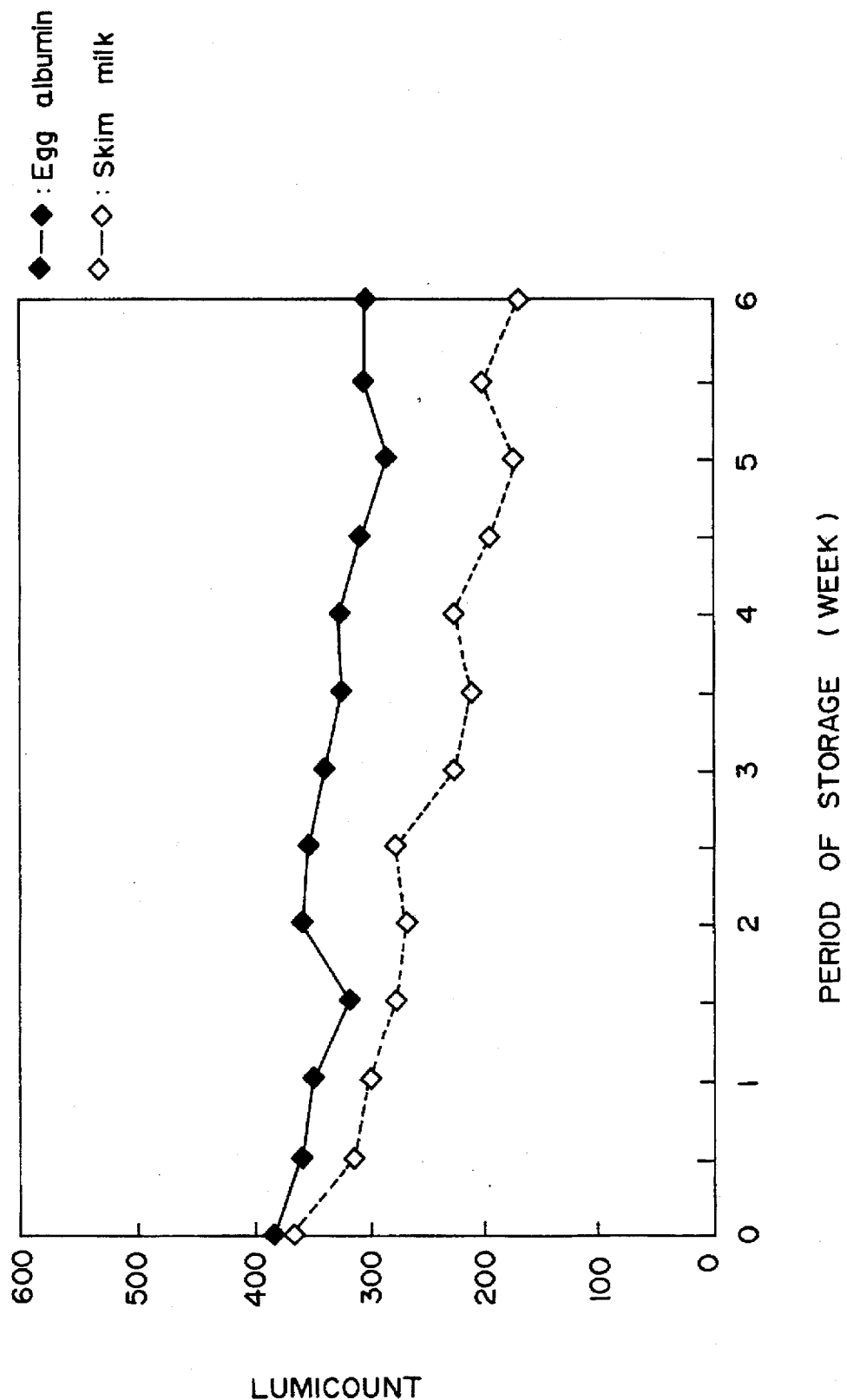
FIG. 4 is a graph showing the storage stability of hydrogen peroxide solutions containing egg albumin and skim milk, respectively.

The chemiluminescent reaction of each of the hydrogen peroxide sample solutions was conducted by diluting 100,000-fold the antiendothelin-1 monoclonal antibody, which had been labelled with the horseradish peroxidase, with the borate, said borate containing 0.075% of egg albumin (product of Seikagaku Kogyo Co., Ltd.), placing a 100 µl portion of the resulting solution in each well of a black-colored module-typed microtiter plate (manufactured by Dynatec, Inc.), adding 8 µl of a 2 mM solution of 4-[4'-(2'-methyl)thiazolyl]phenol in dimethyl sulfoxide, 50 µl of the hydrogen peroxide sample solution and 50 µl of a 20 mM luminol solution successively in this order, and then mixing the contents. Using a chemiluminescence meter, luminescence was measured and the luminescence measured upon an elapsed time of 9 minutes was recorded as a measurement value (FIG. 4). It is understood from FIG. 4 that egg albumin is more effective for the storage stability of a hydrogen peroxide solution than skim milk.

EXPERIMENT 4

Effects of non-ionic surfactant and/or skim milk when various enhancers are used (1) Effects of non-ionic surfactant and/or skim milk on chemiluminescent reaction in the presence of 4-[4'-(2'-methyl)thiazolyl]phenol An experiment was conducted in a similar manner to Experiment 2-3 except that no mannitol was added to the buffer for the chemiluminescent reaction and "Adekatol SO-135" (product of Asahi Denka Kogyo K.K.) was used as a non-ionic surfactant. The noise (N) and signal (S) were then measured likewise (Table 7).

TABLE 7

| Additive | Noise* | Signal* | S/N ratio |
| --- | --- | --- | --- |
| None (control) | 1581 | 1968 | 1.24 |
| Adekatol SO-135 | 1105 | 3043 | 2.75 |
| Skim milk | 135 | 1655 | 12.21 |
| Adekatol SO-135 + skim milk | 131 | 2082 | 15.9 |

*Unit: lumicount (2) Effects of non-ionic surfactant and/or skim milk on chemiluminescent reaction in the presence of 4-[4'-(2'-methyl)thiazolyl]phenol An experiment was conducted as in the above (1) except that 20 mM of 4-[2'-(4'-methyl)thiazolyl]phenol were used as an enhancer instead of 2 mM of 4-[4'-(2'-methyl)thiazolyl]phenol (Table 8).

TABLE 8

| Additive | Noise* | Signal* | S/N ratio |
|---|---|---|---|
| None (control) | 1164 | 1478 | 1.27 |
| Adekatol SO-135 | 948 | 3580 | 3.77 |
| Skim milk | 85 | 493 | 5.80 |
| Adekatol SO-135 + skim milk | 94 | 1114 | 11.9 |

*Unit: lumicount (3) Effects of non-ionic surfactant and/or skim milk in chemiluminescent reaction in the presence of 3-(10-phenothiazyl)-n-propylsulfonate An experiment was conducted as in the above except that 20 mM of a 3-(10-phenothiazyl)-n-propylsulfonate were used as an enhancer instead of 2 mv of 4-[4'-(2'-methyl)thiazolyl]phenol (Table 9).

TABLE 9

| Additive | Noise* | Signal* | S/N ratio |
|---|---|---|---|
| None (control) | 1371 | 1493 | 1.09 |
| Adekatol SO-135 | 942 | 3162 | 3.36 |
| Skim milk | 164 | 1510 | 9.21 |
| Adekatol SO-135 + skim milk | 130 | 1569 | 12.1 |

*Unit: lumicount (4) Effects of non-ionic surfactant and/or skim milk in chemiluminescent reaction in the presence of p-iodophenol An experiment was conducted as in the above except that 10 mM p-iodophenol was used as an enhancer (Table 10).

TABLE 10

| Additive | Noise* | Signal* | S/N ratio |
|---|---|---|---|
| None (control) | 4154 | 4117 | 0.99 |
| Adekatol SO-135 | 1015 | 1997 | 1.97 |
| Skim milk | 149 | 501 | 3.36 |
| Adekatol SO-135 + skim milk | 119 | 420 | 3.52 |

*Unit: lumicount

Using measurement of endothelin-1 as an example, the present invention will hereinafter be described in further detail.

EXAMPLE 1

(1) Calibration Curve For Endothelin-1

Endothelin-1 (hereinafter abbreviated as "ET-1", product of Peptide Institute, Inc.; code number: 4198-s) was diluted as a standard with the calcium-free Dulbecco's phosphate-buffered physiological saline containing 0.1% of Tween 20 and 0.1% of skim milk (hereinafter called "the diluting buffer"), whereby standard endothelin-1 solutions whose concentrations were 2, 5, 10, 20 and 40 pg/ml, respectively, were prepared.

An antiendothelin antibody (product of Immunobiological Laboratories Co., Ltd.; antiendothelin$^{15-21}$ specific antibody; code number: 16155) was diluted beforehand to a concentration of 5 µg/ml with a 50 mM sodium phosphate buffer (pH 7.0). The solution so diluted was poured in 200 µl portions in the individual wells of a black-colored, module-typed microtiter plate (manufactured by Nunc, Inc.; code number: 475515). The diluted solution was allowed to stand overnight at 4° C. so that the antibody was adsorbed on the walls of the individual wells of the plate. Those wells were washed twice with deionized and distilled water, followed by the addition of 400 µl of 0.5% skim milk to each well. The contents of each well was incubated at 37° C. for 6 hours (blocking treatment). Each well was then washed three times with the calcium-free Dulbecco's phosphate-buffered physiological saline containing 0.1% of Tween 20 (hereinafter called "the washing buffer") so that an antibody-immobilized plate was prepared.

The standard solutions of endothelin-1, which had been prepared in advance, were placed in 200 µl portions in the wells of the plate and were then allowed to stand overnight at room temperature. Each well was then washed ten times with the washing buffer, followed by the addition of 200 µl of a solution of a peroxidase-labelled antiendothelin-1 antibody (product of Immunobiological Laboratories Co., Ltd.; code number: 16165). The concentration of the antibody in the solution had been adjusted to 2 µg/ml with the diluting buffer. The reaction mixture so formed was then incubated at 37° C. for 2 hours. After each well was washed ten times with the washing buffer, each well was added with 100 µl of a 50 mM (pH 10) sodium borate buffer, which contained a 2 mM hydrogen peroxide containing 0.1% of Adekatol SO-135 and 0.1% of skim milk and will hereinafter called "the luminescent substrate solution A", and then with 100 µl of a 1:1 (by volume) liquid mixture of a 20 mM luminol solution and a 50 mM (pH 10) sodium borate buffer which contained a 0.32 mM 4-[4'-(2'-methyl)thiazolyl]phenol solution and will hereinafter called "the luminescent substrate solution B". Ten minutes later, luminescence was measured by a chemiluminescence meter. The reagent blank was determined by taking, instead of the standard solutions of endothelin-1, the diluting buffer in the same volume and treating it in a similar manner. Concentrations of endothelin-1 were plotted along the axis of abscissas, while luminescence quantities (lumicounts) were plotted along the axis of ordinates. The data collected through the above procedures were plotted on the graph to obtain a calibration line for endothelin-1 (FIG. 5).

Figure 5:
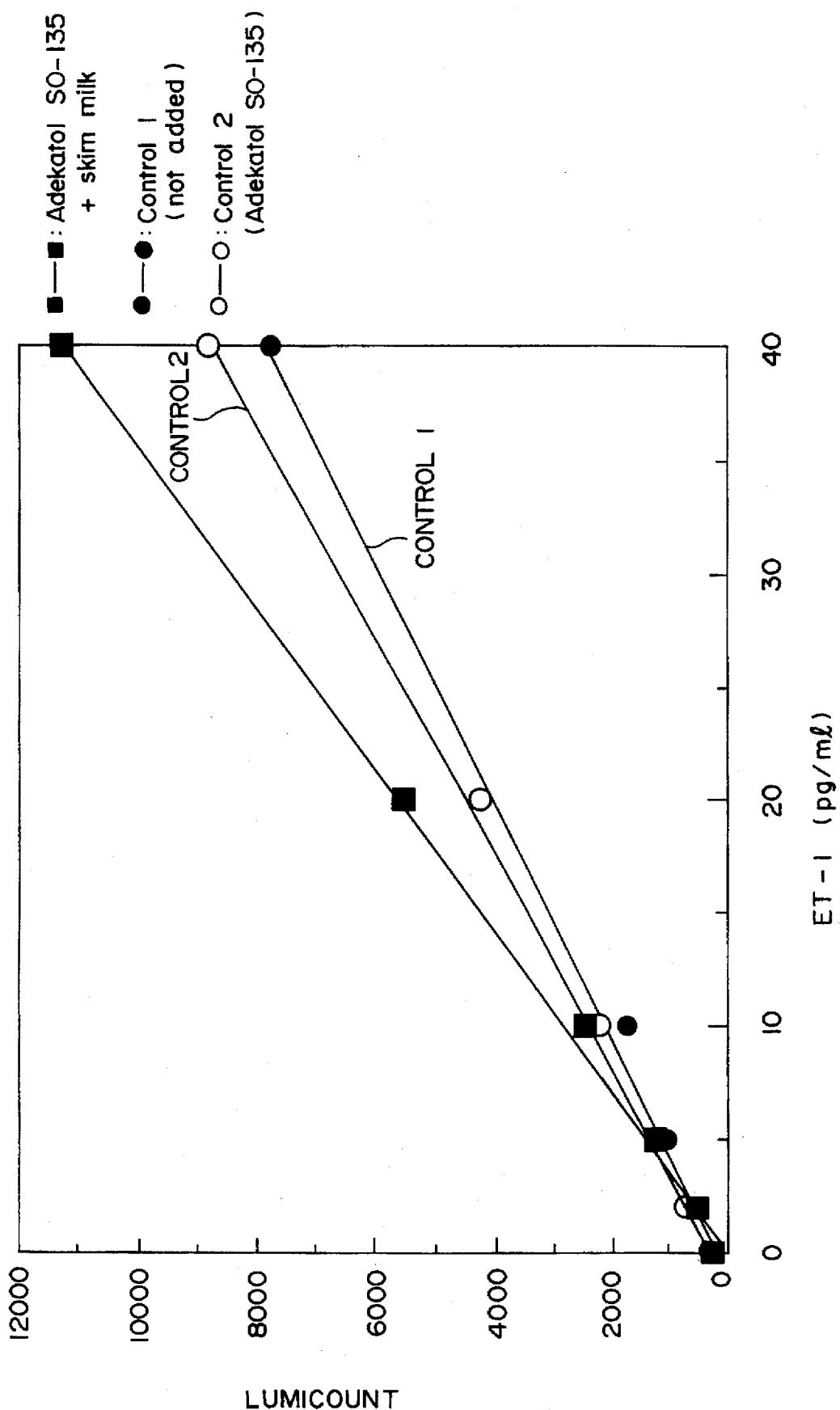
FIG. 5 is a graph showing calibration lines of endothelin.

For the sake of reference, FIG. 5 also shows calibration curves obtained in a similar manner by using, as the luminescent substrate solution A, a 50 mM (pH 10) sodium borate buffer containing a 2 mM hydrogen peroxide solution which contained neither Adekatol SO-135 nor skim milk (Control 1) and a 50 mM (pH 10) sodium borate buffer containing a 2 mM hydrogen peroxide solution which contained 0.1% of Adekatol SO-135 (Control 2), respectively.

It is understood from FIG. 5 that the existence of both Adekatol SO-135 and skim milk in a buffer for luminescent reaction results in an endothelin-1 calibration curve of a large inclination and hence provides high measurement sensitivity.

(2) Measurement of Endothelin-1 in Plasma of Normal Subjects

Endothelin-1 (product of Peptide Institute, Inc.; code number: 4198-s) as a standard was diluted with plasma which was free of endothelin-1, thereby preparing standard endothelin-1 solutions whose concentrations were 2, 5, 10, 20 and 40 pg/ml, respectively.

With respect to the above standard endothelin-1 solutions and samples (plasma of normal subjects: 6 samples), procedures similar to those described above under (1) were conducted so that the quantities of luminescence were determined. From the quantities of luminescence (calibration curve) of the standard endothelin-1 solutions, the concentrations of endothelin-1 in the individual samples of normal subjects were determined (Table 11).

TABLE 11

| Sample No. | ET-1 (pg/ml) | Sample No. | ET-1 (pg/ml) |
|---|---|---|---|
| 1 | 1.47 | 4 | 3.00 |
| 2 | 2.12 | 5 | 2.79 |
| 3 | 1.87 | 6 | 1.55 |

We claim:

1. A chemiluminescent analytical method for measuring the presence and/or amount of an analyte in a sample which comprises the steps, in the following order, of:
  (a) binding a peroxidase as a labelling substance to the analyte via a binding reagent which specifically binds to the analyte so as to label the analyte with the peroxidase;
  (b) isolating the labelled analyte;
  (c) reacting the labelled analyte in an aqueous solution comprising luminol, hydrogen peroxide and chemiluminescent enhancer to produce chemiluminescence, wherein said aqueous solution further contains skim milk, egg albumin, or a combination of skim milk and egg albumin, wherein the skim milk and/or the egg albumin is used in an amount so as to reduce the non-specific chemiluminescent reaction;
  (d) detecting and measuring the chemiluminescence resulting from the reaction in step (c), thereby measuring the presence and/or amount of the analyte in the sample.

2. The method of claim 1, wherein the aqueous solution further comprises a non-ionic surfactant.

3. The method of claim 2, wherein the non-ionic surfactant is a polyoxyethylene ether.

4. The method of claim 1, wherein the aqueous solution further comprises a sugar alcohol.

5. The method of claim 4, wherein the sugar alcohol is mannitol.

6. The method of claim 1, wherein the aqueous solution further comprises a non-ionic surfactant and a sugar alcohol.

7. The method of claim 1, wherein the concentration of the skim milk and/or egg albumin in the aqueous solution ranges from 0.01 wt. % to 1.0 wt. %.

* * * * *